(12) United States Patent
Campillo Ronquillo

(10) Patent No.: US 12,409,194 B2
(45) Date of Patent: *Sep. 9, 2025

(54) COMPOSITIONS AND METHODS FOR TREATING DIABETIC FOOT AND OTHER INJURIES AND SORES

(71) Applicant: XOsmar Industries, LLC, Washington, DC (US)

(72) Inventor: Humberto Ignacio Campillo Ronquillo, Gomez Palacio (MX)

(73) Assignee: XOsmar Industries, LLC, Washington, DC (US)

( * ) Notice: Subject to any disclaimer, the term of this patent is extended or adjusted under 35 U.S.C. 154(b) by 15 days.

This patent is subject to a terminal disclaimer.

(21) Appl. No.: 18/371,087

(22) Filed: Sep. 21, 2023

(65) Prior Publication Data

US 2024/0009251 A1 Jan. 11, 2024

Related U.S. Application Data

(60) Division of application No. 17/210,596, filed on Mar. 24, 2021, now Pat. No. 11,801,270, which is a continuation of application No. 16/990,203, filed on Aug. 11, 2020, now Pat. No. 10,980,844.

(60) Provisional application No. 62/891,449, filed on Aug. 26, 2019.

(51) Int. Cl.
| | | |
|---|---|---|
| *A61K 35/644* | (2015.01) | |
| *A61K 9/70* | (2006.01) | |
| *A61K 36/28* | (2006.01) | |
| *A61K 36/47* | (2006.01) | |
| *A61K 36/53* | (2006.01) | |

(Continued)

(52) U.S. Cl.
CPC .......... *A61K 35/644* (2013.01); *A61K 9/7007* (2013.01); *A61K 36/28* (2013.01); *A61K 36/47* (2013.01); *A61K 36/53* (2013.01); *A61K 36/63* (2013.01); *A61K 47/10* (2013.01)

(58) Field of Classification Search
CPC ..................................................... A61K 35/644
See application file for complete search history.

(56) References Cited

FOREIGN PATENT DOCUMENTS

| JP | 2002047123 A | * | 2/2002 |
| JP | 2010536892 A | * | 12/2010 |
| WO | WO-2018145219 A1 | * | 8/2018 |

* cited by examiner

*Primary Examiner* — Benjamin J Packard
(74) *Attorney, Agent, or Firm* — Mei & Mark LLP

(57) ABSTRACT

In one embodiment, a composition may include beeswax, Candelilla wax, oregano oil, glycerin, olive oil, arnica plant concentrate, and carbolic acid. In another embodiment, a method for treating an injury to an affected limb may include may include cleaning the affected limb, providing a water-based treatment composition, applying the water-based treatment composition to the affected limb, providing an oil-based treatment composition, and applying the oil-based treatment composition to the affected limb. The method may further include providing a gauze impregnated with a wax-based treatment composition and wrapping the impregnated gauze around the affected limb. The water-based treatment composition may include water, essence of oregano, and carbolic acid. The oil-based treatment composition may include glycerin, arnica plant concentrate, and carbolic acid. The wax-based treatment composition may include beeswax, Candelilla wax, arnica plant concentrate, and carbolic acid.

19 Claims, 23 Drawing Sheets

(51) Int. Cl.
*A61K 36/63* (2006.01)
*A61K 47/10* (2017.01)

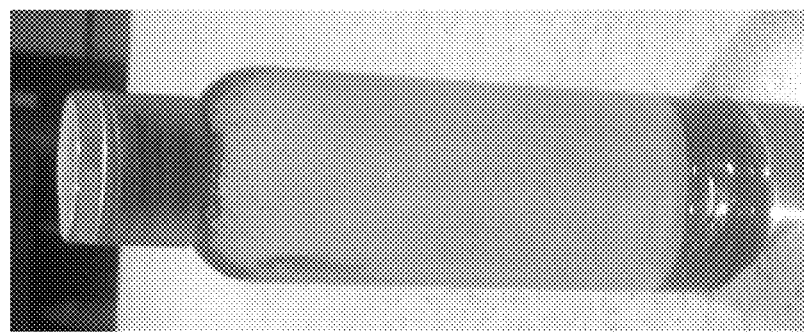
FIG. 2D
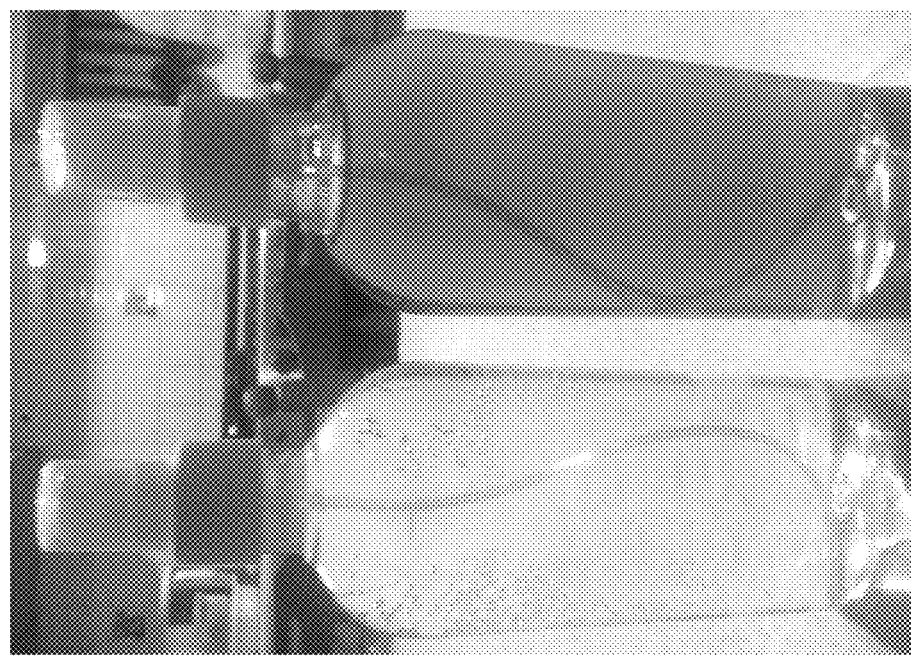
FIG. 2C
FIG. 2B
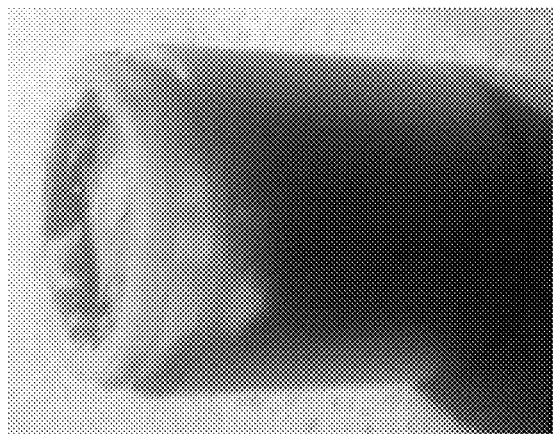
FIG. 2A
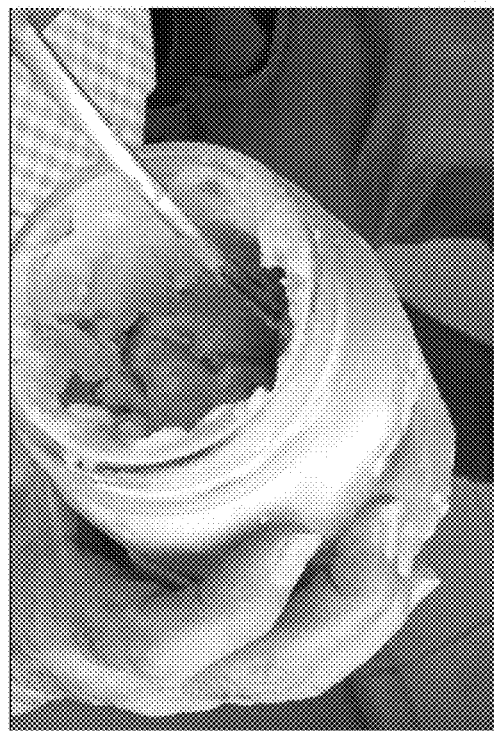
FIG. 2E

COMPOSITIONS AND METHODS FOR TREATING DIABETIC FOOT AND OTHER INJURIES AND SORES

This application claims priority to U.S. Provisional Patent Application Ser. No. 62/891,449, filed on Aug. 26, 2019, the disclosure of which is hereby incorporated by reference in its entirety.

TECHNICAL FIELD

This disclosure relates to compositions and methods for treating wounds and other injuries. More particularly, this disclosure relates to treating diabetic foot, its complications, sores, other skin ailments, and/or other maladies via applications of wax-based, water-based, and/or oil based treatment composition(s) to an affected area, the compositions, and methods of manufacture thereof.

BACKGROUND

Diabetic foot is a complication associated with diabetes mellitus. It is commonly associated with infections, foot ulcers, severe skin problems, and joint degeneration. Diabetic foot and its associated conditions are often painful and debilitating, and sometimes require amputation of portions of the foot or leg. Currently, treatment for diabetic foot includes antibiotics, topical dressings, and orthopedic appliances. Treatment is often challenging, prolonged, and expensive; yet for many patients, such treatments are ineffective.

Similarly, treatment for open wounds, bed sores, other skin sores, and other skin related ailments may be challenging, prolonged, expensive, and/or ineffective.

Thus, a need exists for new, effective treatments for diabetic foot, its associated conditions, skin sores, and other injuries. It may be advantageous for such new treatments to be economical. Further, it may be desirable for compositions associated with such new treatments to be entirely or substantially comprised of natural and/or organic ingredients.

SUMMARY

The present disclosure provides a description of compositions, kits thereof, methods of use thereof, and methods of manufacture thereof, to address the perceived problems described above.

In one embodiment, a composition is provided. The composition may include beeswax, oregano oil, glycerin, a base oil, arnica plant concentrate, and carbolic acid. The composition may further include Candelilla wax.

For each 1Kg of beeswax, the composition may include 24-36 g of Candelilla wax, 4-6 ml of oregano oil, 80-120 ml of glycerin per 1 Kg of beeswax, 40-120 ml of base oil, 2.4-6 ml of arnica plan, and 5-12 ml of carbolic acid. The base oil may comprise or substantially consist of olive oil. More narrowly, for each 1 Kg of beeswax, the composition may include 27-33 g of Candelilla wax, 4.5-5.5 ml of oregano oil, 90-110 ml of glycerin, 45-110 ml of base oil, 2.7-5.5 ml of arnica plant concentrate, and 5.5-11 ml of carbolic acid. Even more narrowly, for each 1 Kg of beeswax, the composition may include 28.5-31.5 g of Candelilla wax, 4.75-5.25 ml of oregano oil, 95-105 ml of glycerin, 47.5 -105 ml of base oil, 2.85-5.25 ml of arnica plant, and 6-10.5 ml of carbolic acid. The composition may further include 8-12 g of Propolis per 1 Kg of beeswax.

A bandage may be impregnated with the composition. The bandage may be impregnated with 3 g-10 g of the composition. The bandage may be medical grade gauze.

In another embodiment, a method of making a medical composition is provided. The method may include melting a portion of beeswax, adding a portion of Candelilla wax to the portion of melted beeswax to form a mixture, adding a portion of base oil to the mixture, adding a portion of glycerin oil to the mixture, adding a portion of carbolic acid to the mixture, adding a portion of arnica plant concentrate to the mixture, and adding a portion of oregano oil to the mixture. The method may further include impregnating a bandage with the mixture.

The portion of Candelilla wax may be 24-36 g of Candelilla wax per 1 Kg of beeswax. The portion of oregano oil may be 4-6 ml of oregano oil per 1 Kg of beeswax. The portion of glycerin may be 80-120 ml of glycerin per 1 Kg of beeswax. The portion of base oil may be 40-120 ml of vegetable oil per 1 Kg of beeswax. The portion of arnica plant concentrate may be 2.4-6 ml of arnica plant concentrate per 1 Kg of beeswax. The portion of carbolic acid may be 8-12 ml of carbolic acid per 1 Kg of beeswax. The vegetable oil may substantially consist of or comprise olive oil.

The portion of Candelilla wax may be 27-33 g of Candelilla wax per 1 Kg of beeswax. The portion of oregano oil may be 4.5-5.5 ml of oregano oil per 1 Kg of beeswax. The portion of glycerin may be 90-110 ml of glycerin per 1 Kg of beeswax. The portion of base oil may be 45-110 ml of base oil per 1 Kg of beeswax. The portion of arnica plant concentrate may be 2.7-5.5 ml of arnica plant concentrate per 1 Kg of beeswax. The portion of carbolic acid is 9-11 ml of carbolic acid per 1 Kg of beeswax.

In yet another embodiment, a method for treating an injury to an affected limb is provided. The method may include cleaning the affected limb, providing a water-based treatment composition, applying the water-based treatment composition to the affected limb, providing an oil-based treatment composition, and applying the oil-based treatment composition to the affected limb. The method may further include providing a gauze impregnated with a wax-based treatment composition and wrapping the impregnated gauze around the affected limb.

The water-based treatment composition may include water, essence of oregano, and carbolic acid. The oil-based treatment composition may include glycerin, arnica plant concentrate, and carbolic acid. The wax-based treatment composition may include beeswax, Candelilla wax, arnica plant concentrate, and carbolic acid. The water-based treatment composition may further include arnica plant concentrate. The wax-based treatment composition may further include oregano oil and olive oil.

Applying the water-based treatment composition may further include administering 3-10 ml of water-based treatment composition to the affected limb, smearing the water-based treatment composition until at least the injury is covered, and allowing the water-based treatment to dry. The affected limb may be covered from at least the knee to the bottom of the foot.

Applying the oil-based treatment composition may further include administering 1-3 ml of oil-based treatment composition to the affected limb, and smearing the oil-based treatment composition until at least the injury is covered. The affected limb may be covered from at least the knee to the bottom of the foot. Wrapping the impregnated gauze around the affected limb further may further include covering the affected limb with the gauze from at least the knee to the bottom of the foot. Providing the gauze impregnated with a wax-based treatment composition may further include impregnating 3-10 g wax-based treatment composition into a gauze.

In yet another embodiment, a medical treatment kit is provided. The kit may include a water-based treatment composition, an oil-based treatment composition, and a wax-based treatment composition. The water-based treatment composition may include water, essence of oregano, and carbolic acid. The oil-based treatment composition may include glycerin, arnica plant concentrate, and carbolic acid. The wax-based treatment composition may include beeswax, Candelilla wax, arnica plant concentrate, and carbolic acid.

The medical treatment kit treatment may further include a bandage. At least a portion of the wax-based treatment composition may be impregnated in the bandage.

The wax-based treatment composition may further include oregano oil and the base oil may include olive oil. The water-based treatment composition may further include arnica plant concentrate.

The wax-based treatment composition may include 24-36 g of Candelilla wax per 1 Kg of beeswax, 4-6 ml of oregano oil per 1 Kg of beeswax, 80-120 ml of glycerin per 1 Kg of beeswax, 40-120 ml of base oil per 1 Kg of beeswax, 2.4-6 ml of arnica plant concentrate per 1 Kg of beeswax; and 5-12 ml of carbolic acid per 1 Kg of beeswax.

BRIEF DESCRIPTION OF THE DRAWINGS

The accompanying drawings, which are incorporated into and constitute a part of this disclosure, illustrate several embodiments and aspects of the compositions, and methods described herein and, together with the description, serve to explain the principles of the invention.

FIGS. 1A-1E are a progression of photos illustrating treatment of diabetic foot, in accordance with exemplary embodiments.

FIGS. 2A and 2E are photos of a wax-based treatment composition, in accordance with exemplary embodiments.

FIG. 2B-2C are photographic images of water-based treatment compositions, in accordance with exemplary embodiments.

FIG. 2D is a photo of an oil-based treatment composition, in accordance with exemplary embodiments.

DETAILED DESCRIPTION

In a non-limiting example, one or more the disclosed compositions in one or multiple versions or variations may be used to treat diabetic foot. In some embodiments, the disclosed compositions may be used to for treatment of bed sores (pressure ulcers), open wounds, extreme dry skin, cracked skin on feet and hands, skin infections, herpes sores, other types of skin sores, and/or other maladies. It is also contemplated that the disclosed compositions may be used to treat sciatica, muscle pain, other pain, circulation issues, and/or other medical conditions that would be recognized by a person of skill in the art.

Wax-Based Treatment Composition Embodiments

With reference to FIG. 2A and 2E, a wax-based treatment composition embodiment may be provided. The wax-based treatment composition may comprise one or more of beeswax, preferably natural; food grade Candelilla wax; oregano oil; glycerin, preferable organic; olive oil; Arnica plant concentrate, and carbolic acid (Phenol).

The Candelilla wax is believed to enhance the consistency and penetration characteristics of wax-based treatment compositions. Quicker penetration of the active compounds with anti-fungal and anti-bacterial properties into the wound may prevent worsening of an infection, speed up the clearing up of an infection, which may in turn provide more regeneration capacity to the infected tissue, and/or speed up healing of the wound. The oregano oil and/or olive oil, especially when used in combination with Candelilla wax and/or together, are believed to be effective in fighting infection, including infections associated with gangrene.

In some embodiments, beeswax may be selected based on the type of flowers the bees producing the wax predominantly feed from. For example, the beeswax may be arnica beeswax or mesquite beeswax. In certain embodiments, arnica beeswax may be preferred.

Figure 10:
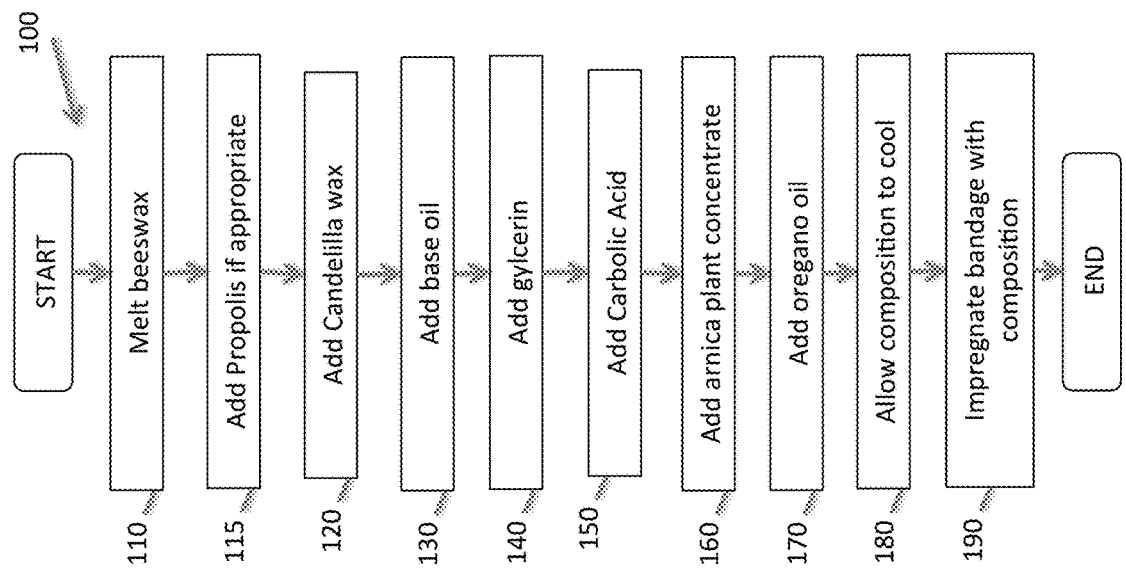
FIG. 10 is a flowchart of a method of preparing wax-based treatment composition embodiments, in accordance with exemplary embodiments.

In one embodiment, the above-referenced ingredients may be combined to arrive at the wax-based treatment composition in the following relative amounts:

Beeswax (Cera de abeja)—1 Kg
Candelilla wax food grade (Cera de Candelilla con valor alimentación)—30 g
Oregano oil (Aceite de Orégano)—5ml
Organic glycerin (Glicerina Orgánica)—100 ml
Olive oil (Aceite de Oliva)—50-100 ml
Arnica plant concentrate (Concentrado de planta de Árnica)—3-5 ml
Carbolic acid (Ácido Fenico)—6-10 ml Consistent with the above listing of ingredients and amounts, a wax-based treatment composition may be prepared by embodiments of method 100, as outlined in FIG. 10. As in step 110, the beeswax may be melted. As in step 120, the Candelilla wax may be added to the melted beeswax. Heat may be applied until all of the waxes are completely melted. After melting has been completed, as in step 130, the base oil may be added and mixed until the wax is malleable and easily spreadable on gauze or other fabric that may be applied to a wound. In preferred embodiments, the base oil may substantially consist of and/or comprise olive oil. However, the base oil may additionally or alternatively comprise vegetable oils and/or other suitable oils or compounds known in the art to (i) be safe for human consumption and/or medical use and (ii) improve the malleability of wax. Accordingly, the amount of base oil added may vary depending on the malleability and/or other characteristics of the beeswax utilized. As in steps 140 and 150, glycerin and Carbolic acid may be added, preferably in that order. As in steps 160 and 170, arnica plant concentrate and oregano oil may be added. As in step 180, the composition may be permitted to cool. Preferably, the composition should be continually mixed from at least after the time the base oil has been added and until the composition has cooled.

In some embodiments, the wax-based treatment composition may be impregnated into gauze other bandage fabric during the manufacturing process as in step 190. In some corresponding manufacturing methods, cooling step 180 may be omitted, may occur after step 190, and/or may occur partially before and partially after step 190. Accordingly, in such embodiments, the distribution of wax-based treatment compositions that are already pre-impregnated in gauze or other fabrics may allow medical providers or patients to omit the impregnation step during treatments described below.

In some embodiments, Propolis (Propóleo), for example, at or around 30 g with reference to the above listed relative amounts, may be added to the melted beeswax. Propolis may be naturally present in beeswax and may result in the melted beeswax to turn black or otherwise darken when heated. The presence of Propolis in the wax-based treatment composition is believed to improve or otherwise enhance its effectiveness. If the melted beeswax does not sufficiently darken during the corresponding steps of the wax-based treatment composition, additional Propolis may be added as in step 115.

Water-Based Treatment Composition Embodiments

With reference to FIG. 2B, an arnica-free water-based treatment composition may be provided. The arnica-free water-based treatment composition may comprise one or more of distilled water, essence of oregano, and carbolic acid (Phenol). In an exemplary embodiment, the above-referenced ingredients may be mixed to arrive at the water-based treatment composition in the following relative amounts:

Distilled water (Agua destilada)—1 liter
    Essence of Oregano (Esencia Orégano)—0.16907 US Fluid Ounces (5 ml)
    Carbolic acid (Ácido Fenico)—2-3 drops (approximately 1.5-2 ml)

With reference to FIG. 2C, an arnica-inclusive water-based treatment composition may be provided. The arnica-inclusive water-based treatment composition may comprise one or more of distilled water, essence of oregano, arnica plant concentrate, and carbolic acid (Phenol). In an exemplary embodiment, the below-referenced ingredients may be mixed to arrive at the arnica-inclusive water-based treatment composition in the following relative amounts:

Distilled water (Agua destilada)—1 liter
    Essence of Oregano (Esencia Orégano)—2-3 ml (or 3-6 ml in alternative embodiments)
    Arnica plant concentrate (Concentrado de planta de Árnica)—2-3 ml (or 3-6 ml in alternative embodiments)
    Carbolic acid (Ácido Fenico)—2-3 drops (approximately 1.5-2 ml)

Oil-Based Treatment Composition Embodiments

With reference to FIG. 2D, an oil-based treatment composition may be provided. The oil-based treatment composition may comprise one or more of glycerin, preferable organic; Arnica plant concentrate, and carbolic acid (Phenol). In an exemplary embodiment, the above-referenced ingredients may be mixed to arrive at the oil-based treatment composition in the following relative amounts:

Organic glycerin (Glicerina Orgánica)—1 liter
    Arnica plant concentrate (Concentrado de planta de Árnica)—5 ml
    Carbolic acid (Ácido Fenico)—2-3 ml Preferably, the above-described compositions should be stored in a clean, dark place at or around room temperature.

As may be appreciated by a person of skill in the art with respect to all composition versions described above, in alternative embodiments, the relative amounts of one or more of the above listed ingredients may be altered; furthermore, one or more of the above listed ingredients omitted or substituted for one or more compositions or mixtures with similar properties or functions. Generally, in related embodiments, the relative ingredient amounts may vary by up to 5%, 10%, or 20% and still substantially achieve their intended purposes.

Arnica plant concentrate may be derived via the following method: A raw, preferably fresh, arnica plant may be washed. The washed arnica plant, including stems and flowers, may be milled, for example, with a mortar and pestle, such as a molcajete, or by other known methods in the art. Then, the milled plant material may be placed into a container with water. In exemplary embodiments, approximately 2 liter of waters may be used for each 1 kg of milled arnica plant. The water may then be boiled. Then, arnica plant concentrate may be derived via a distillation process, as would be known to persons of skill in the art.

In certain embodiments, the distillation process may comprise boiling the arnica-laden water until only a relatively small amount of very dark liquid remains at the bottom of the pot. This very dark liquid comprises the arnica plant concentrate, which it is believed to comprise approximately 80% arnica compounds.

Figure 7C:
FIGS. 7B-7C are photos illustrating aspects of impregnating a gauze with a wax-based treatment composition, in accordance with exemplary embodiments.
Figure 7B:
Figure 7A:
FIG. 7A is a photo illustrating an aspect of preparing arnica plant concentrate, in accordance with exemplary embodiments.

To efficiently remove the arnica plant concentrate from the pot with minimal waste, a portion of oil may be added to dark residual liquid. Preferably, sunflower oil or another vegetable oil may be used. In certain embodiments, approximately 100 ml sunflower oil may be added for each 1 kg fresh arnica used. The contents of the pot may be agitated and poured out. The mixture may be strained to remove remaining plant material. Finally, the mixture may be permitted to rest so that the oil may separate from the arnica plant concentrate, for example as shown in FIG. 7. In some embodiments, a glass flask may preferably be used for this step. After separation, the oil may be poured off and discarded, leaving only the dark arnica plant concentrate. Each 1 kg of milled arnica plant processed via embodiments disclosed above may yield approximately 10-20 ml arnica plant concentrate, as that term is used in the composition ingredient listings provided above.

In preferred embodiments, arnica plant concentrate at or about an 80% concentration may be used in preparing the above-disclosed treatment compounds. However, as would be appreciated by a person of ordinary skill in the art, if arnica plant concentrate or a similar substitute arnica ingredient is derived via other methods and/or commercially purchased, it may have a different concentration. Amounts of a substitute arnica ingredient used to make a treatment composition should be selected as to result in a substantially similar amount and/or concentration of arnica compounds in treatment composition embodiments disclosed herein. For example, if a substitute arnica ingredient is more concentrated that 80%, less may be included; if a substitute arnica ingredient is less concentrated than 80%, more may be included.

Treatment Method Embodiments

In certain embodiments, diabetic foot, associated maladies, and/or other ailments may be treated by application of multiple versions of the above-described treatment composition embodiments.

Figure 11:
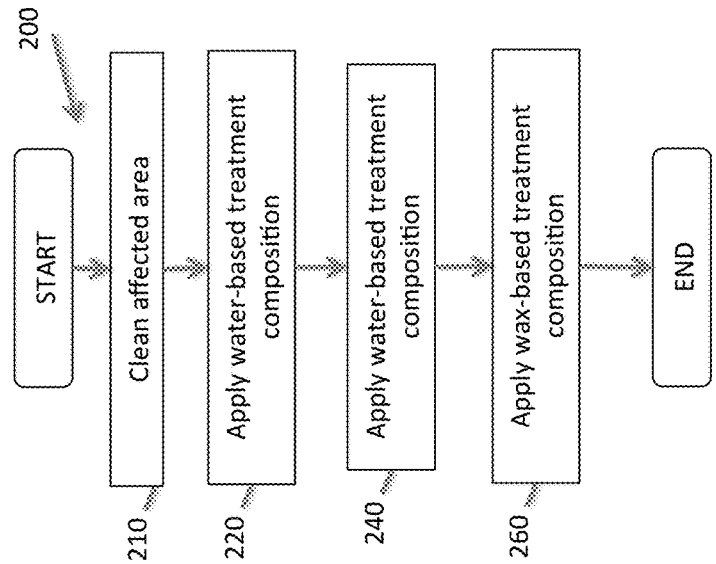
FIG. 11 is a flowchart of a method of treatment, in accordance with exemplary embodiments.

With reference to FIG. 11, general treatment method 200 is provided. As would be understood by persons of ordinary skill in the art after reviewing the instant disclosure, certain steps may be omitted, modified, and/or occur in an alternative order in various embodiments, depending, in part on the nature and severity of the malady.

As in step 210, treatment may include first thoroughly cleaning the affected area. In certain embodiments, the affected limb at least from the knee and down with soap and water. The patient may, for example, conduct such cleaning in the shower.

As in step 220, at least one water-based treatment composition may be applied. For example, the arnica-free water-based treatment composition and/or arnica-inclusive water-based treatment composition and/or may be applied. Generally, use of the arnica-inclusive water-based treatment composition may be preferred in cases of severe injury and/or tissue damage. For example, where there is an open wound with infection and pus and/or pain, use of the arnica-inclusive water-based treatment composition may be preferred. It is understood that the arnica promotes wound closure, and/or cicatrization. In some embodiments, approximately 4-10 ml of water-based treatment composition may be used daily. In certain preferred embodiments, the water-based treatment composition may be sprayed on, followed by being smeared along the entire treatment area.

In certain exemplary embodiments, the water-based treatment composition(s) may be applied from at least the knee to the end of the foot on the affected limb in each or some applications, for example, in a nighttime application before the patient goes to bed. It is believed that application of the disclosed compound to the lower portion of the leg in addition to the acutely affected area may improve circulation, and accordingly may further promote healing of the wound. Additionally, in preferred embodiments, the applied water-based treatment composition may be permitted to dry before proceeding to step 240.

As in step 240, following the application of the water-based treatment composition(s), the oil-based treatment composition may be applied. In some embodiments, approximately 1-6 ml of oil-based treatment composition may be used daily. The amount used may depend on the size of the wound. For example, where a wound is particularly large, 4 ml-10 ml of oil-based treatment composition may be used daily. In certain preferred embodiments, the oil-based treatment composition may be smeared along the entire treatment area. In exemplary embodiments, the oil-based treatment composition may be applied from at least the knee to the end of the foot on the affected limb in each or some applications, for example, in a night time application before the patient goes to bed.

As in step 260, following the application of the oil-based treatment composition, in some embodiments, for example, where there is a surface infection and/or a wound has substantially closed, a portion of wax-based treatment composition may be incorporated into gauze. The entire treatment area may then be wrapped with the wax-based treatment composition-impregnated gauze. However, the wax-based treatment composition will preferably cover only the wound and a limited area surrounding it. In certain embodiments, the impregnated gauze may be applied to cover the affected limb from at least the knee to the end of the foot. In some embodiments, approximately 4 g-10 of wax-based treatment composition should be used daily.

In certain embodiments, the wax-based treatment composition may not be evenly spread throughout the impregnated gauze, but may rather be concentrated in an area of the gauze that is intended to cover the wound. In certain preferred embodiments, the wax-based treatment composition-impregnated gauze may be prepared and applied by (a) fully opening the gauze to a single layer; (b) applying an appropriate amount of wax-based treatment composition to a portion of the gauze; (c) spreading the wax-based treatment composition into a patch sufficient to cover the wound, for example as shown in FIG. 7B; (d) folding over the single gauze layer such that the wax-based treatment composition patch is sandwiched between two layers of gauze, for example as shown in FIG. 7C; (e) applying the gauze such that the wax-based treatment composition patch covers the wound; and (f) wrapping the remainder of the gauze to secure it. Impregnating the wax-based treatment composition in gauze in this manner enables the wax-based treatment composition to heal the wound while facilitating removal of the wax-based treatment composition from the wound after use. For example, a layer of gauze between the composition and the wound may enable quick removal of the composition from the wound and reduce and/or eliminate the need to remove old wax-based treatment composition from the wound during a cleaning process. A layer of gauze on the outside of the composition may ensure that it stays in place and in contact with the wound during treatment. Portions of the gauze with minimal or no composition impregnation may allow air exposure to other portions of an injured patient's body.

Method 200 may be completed.

After application of treatment composition(s), it may be recommended that the foot remain uncovered (with the exception of the gauze). If necessary, the patient may use flip-flops to ambulate.

Figure 1B:
Figure 1A:

In a first treatment example, a progression of results is sequentially depicted in FIGS. 1A-1E. FIG. 1A depicts the foot of a patient suffering from diabetic foot, including a foot ulcer on the big toe, prior to treatment. In this example, the subject patient was treated daily with 4 ml arnica-free water-based treatment composition; followed by 2 ml oil-based treatment composition; and a gauze impregnated with 4 g wax-based treatment composition—all applied as described above. Approximately, 12-15 days has passed between each respective photograph. Ultimately, dramatic healing may be observed in the progressive photographs, with wound being substantially gone in FIG. 1E.

Figure 3B:
FIGS. 3A-3B are another progression of photos illustrating treatment of diabetic foot, in accordance with exemplary embodiments.
Figure 3A:

In a second treatment example, a progression of results is sequentially depicted in FIGS. 3A-3B. FIG. 3A depicts the foot of a patient suffering from diabetic foot, including an open wound on top of the foot below the middle toe. Prior to FIG. 3A, the patient was being treated daily with 4 ml arnica-free water-based treatment composition, followed by 4 ml arnica-inclusive water-based treatment composition, and followed by 2 ml oil-based treatment composition—all applied as described above. It is believed that these composition applications caused an internal infection to come to the surface of the top of the foot, where it could, in turn, be more effectively treated. After the open, infected wound appeared, the patient was treated with 4 ml arnica-inclusive water-based treatment composition, followed by 2 ml oil-based treatment composition, and a gauze impregnated with between 4 g and 8 g wax-based treatment composition—all applied as described above. Approximately, 12-15 days has passed between FIG. 3A and 3B. Ultimately, dramatic healing may be observed in the progressive photographs, with wound being substantially gone and converted to scar tissue in FIG. 3B.

Figure 4A:
FIGS. 4A-4D are yet another progression of photos illustrating treatment of diabetic foot, in accordance with exemplary embodiments.
Figure 4B:
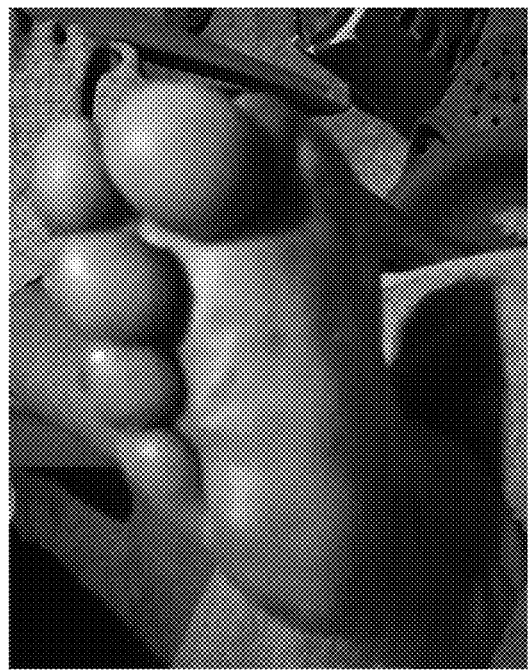
Figure 4C:
Figure 4D:
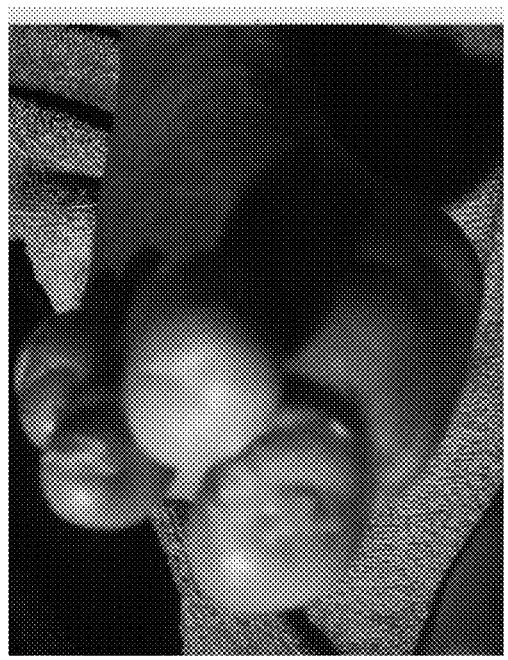

In a third treatment example, a progression of results is sequentially depicted in FIGS. 4A-4D. FIG. 4A depicts the foot of a patient suffering from diabetic foot, including foot ulcers, during an early stage of treatment. The foot was purple at the time treatment began. In this example, the subject patient was treated daily with 4 ml arnica-free water-based treatment composition, followed by 2 ml oil-based treatment composition—all applied as described above. Because no open wound or infection was visible, the wax-based treatment composition was not used. Approximately, 10-12 days has passed between each respective photograph. Healing may be observed in the progressive photographs. After 29 days of treatment, the diabetic foot and related foot ulcers had completely healed.

Figures 5A, 5B, 5C, 5D:
FIGS. 5A-5D are photos illustrating an aspect of treatment of diabetic foot, in accordance with exemplary embodiments.

In a fourth treatment example, a foot with treatment in progress is depicted in FIGS. 5A-5D. FIG. 5A and 5B depict the top of the foot. FIGS. 5C and 5D depict the bottom of the foot where the wound is. In this example, the subject patient was treated daily with 4 ml arnica-free water-based treatment composition; followed by 2 ml oil-based treatment composition; and a gauze impregnated with 4 g wax-based treatment composition—all applied as described above.

Figure 6B:
FIGS. 6A-6D are yet another progression of photos illustrating treatment of diabetic foot, in accordance with exemplary embodiments.
Figure 6A:
Figure 6D:
Figure 6C:

In fifth treatment example, a progression of results is sequentially depicted in FIGS. 6A-6D. FIG. 6A depicts the leg and foot of a patient suffering from severe diabetic foot, including a large, open ulcer extending up the patient's leg, prior to treatment. In this example, the subject patient was treated daily with 4 ml-10 ml arnica-free water-based treatment composition and a gauze impregnated with 4 g-10 g wax-based treatment composition. The amounts of the respective compositions applied each day varied based on how it spread and was absorbed into the skin, and accordingly with the general dryness and/or other skin characteristics at the time of application. There was no infection in this example, but due to the nature of the wound, excessive touching of the wound was avoided. Accordingly, the water-based treatment was sprayed on without any smearing and no oil-based treatment composition was applied.

Approximately 10-12 days has passed between each respective photograph. Dramatic healing may be observed in the progressive photographs, but as may be observed, additional healing is required after FIG. 6D.

Figure 8B:
FIGS. 8A-8E are progression of photos illustrating treatment of extreme dry skin, in accordance with exemplary embodiments.
Figure 8A:
Figure 8D:
Figure 8E:
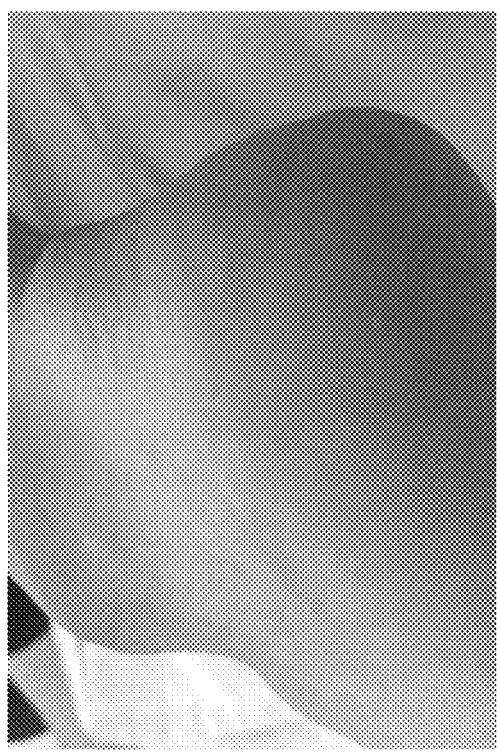
Figure 8C:

In a sixth treatment example, a progression of results is sequentially depicted in FIGS. 8A-8E. FIGS. 8A and 8B depict the heel of patient suffering from extreme dry skin on her heel prior to treatment. In this example, the subject patient was treated daily with 3 g-5 g of wax-based treatment composition directly applied to the skin. In this example, wax-based treatment composition was applied in the evening and rubbed into the heel in a manner similar to the application of an ordinary moisturizer lotion. In certain embodiments, the amount of daily application may vary based on how it the composition spreads on the skin and how it is absorbed into the skin; accordingly, the amount applied may vary with the general dryness and/or other skin characteristics at the time of application. Approximately 12-15 days has passed between each of FIGS. 8A-8E, except FIGS. 8A and 8B were taken on the same day and approximately 8-12 days passed between FIGS. 8C and FIG. 8D. Dramatic improvement in extreme dry skin may be observed in the progressive photographs, and the extreme dry skin has been substantially cured in FIG. 8E. Cracked skin on the feet, hands, and/or other locations may be treated in an identical or substantially similar manner.

Figure 9B:
FIGS. 9A-9J are yet another progression of photos illustrating treatment of diabetic foot, in accordance with exemplary embodiments.
Figure 9A:

In a seventh treatment example, a course of treatment of approximately 120 days is sequentially depicted in FIGS. 9A-9J. FIG. 9A depicts, the leg and foot of a patient suffering from severe diabetic foot and whose foot was partially amputated and prior to the beginning of treatment. In FIG. 9A, the amputation wound was initially covered in wax-based treatment composition. While in many embodiments, wax-based treatment composition is not applied until a wound is partially healed and ready for cicatrization, in this example, the wax-based treatment composition was directly applied prior to the treatment regimen described below.

After the wax-based treatment composition application of FIG. 9A, the subject patient was treated twice per day (e.g., morning and night) with 4 ml-10 ml arnica-inclusive water-based treatment composition and 3 ml-5 ml oil-based treatment composition in each application. This first phase of treatment continued until the amputation wound was substantially closed and lasted for approximately 30 days. FIGS. 9A-9C show a progression of healing during this first phase, and approximately 10-15 days passed between each of FIGS. 9A-9C. During this first phase, the affected area was kept clean between applications. The open wound was also kept moist via application of water-based treatment composition to gauze covering the open wound, as shown in FIG. 9K. In some embodiments, such a wet gauze or other fabric may be kept in place with a tubular net bandage, stretch net dressing, and/or the like, especially when the patient is going to sleep.

Figure 9D:
Figure 9C:
Figure 9F:
Figure 9E:
Figure 9H:
Figure 9G:

A second phase of treatment began between FIGS. 9C and 9D. Approximately 5-8 days passed between FIGS. 9C and 9D. As may be observed, FIG. 9D displays less scabbing and pus than FIG. 9C. This is because application and removal of a bandage impregnated with the wax-based treatment composition may beneficially remove scabbing, pus, and/or other healing byproducts.

Figure 9J:
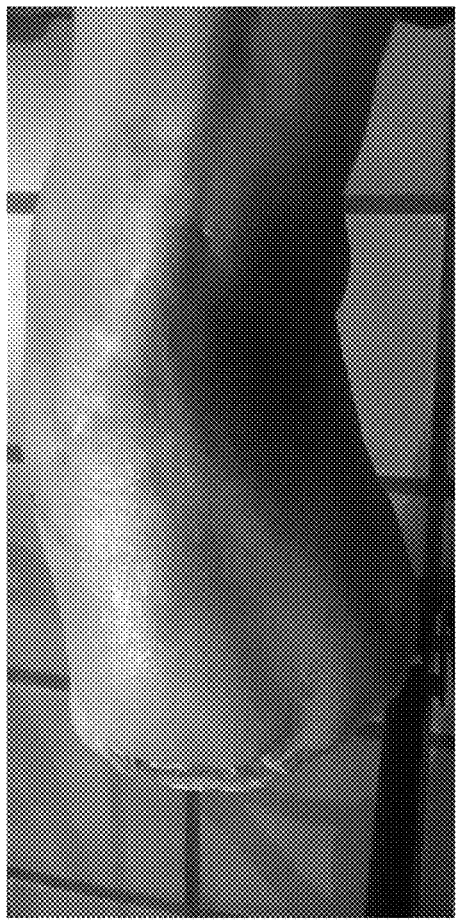
Figure 9K:
FIG. 9K is a photo illustrating a technique for treating an open wound with a water-based treatment composition, in accordance with exemplary embodiments.
Figure 9I:
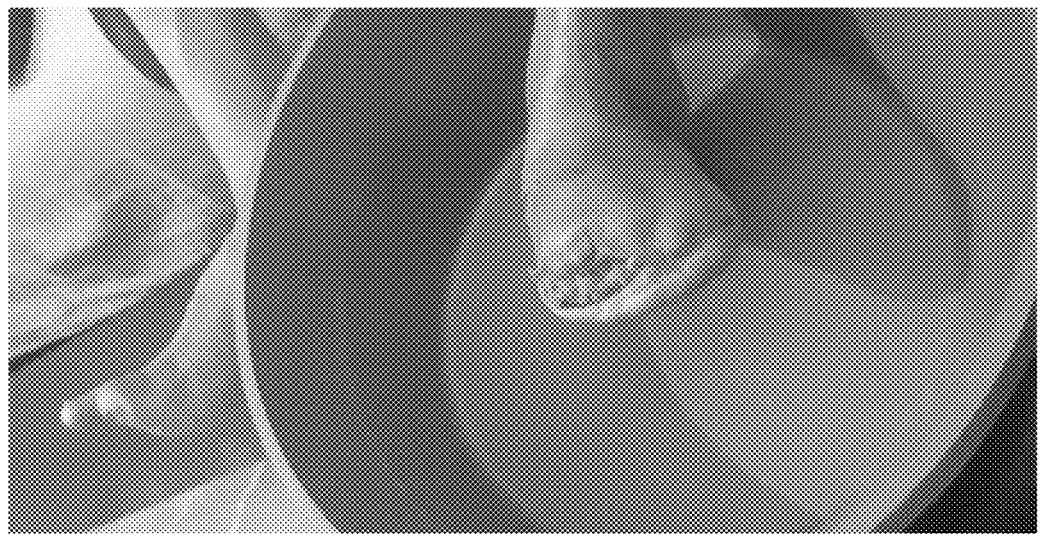

FIGS. 9D-9J show a progression of healing during this second phase of treatment, and approximately 10-15 days passed between each of FIGS. 9D-9J. In the second phase of treatment, the affected area was treated 2-4 times per day (typically 2-3 times per day). Approximately 3 ml-5 ml arnica-inclusive water-based treatment composition and 4 ml-10 ml oil-based treatment composition was used in each application. Also in the second treatment phase, the affected area was wrapped in a gauze impregnated with 4 g-6 g wax-based treatment composition after the last application of water-based and oil based treatment composition each day. FIG. 9J depicts the dramatically healed amputated foot after approximately 90-100 days of treatment with the wax-based treatment composition.

Figure 12B:
FIGS. 12A-12I are yet another progression of photos illustrating treatment of diabetic foot, in accordance with exemplary embodiments.
Figure 12A:
Figure 12D:
Figure 12C:
Figure 12F:
Figure 12E:

In an eighth treatment example, a progression of treatment results is sequentially depicted in FIGS. 12A-12I. FIG. 12A depicts the foot of a patient suffering from moderate diabetic foot. With reference to FIGS. 12A-12D, the affected area was treated 3-4 times per day in a first phase. In this first phase, approximately 1 ml-3 ml arnica-inclusive water-based treatment composition and 3 ml-5 ml oil-based treatment composition was used in each application. This first phase lasted approximately 3 weeks until the wounds were substantially closed.

Figures 12G, 12H, 12I:
Figure 13A:
FIGS. 13A-13H are a progression of photos illustrating treatment of a bed sore, in accordance with exemplary embodiments.
Figure 13B:
Figure 13C:
Figure 13D:
Figure 13F:
Figure 13H:
Figure 13E:
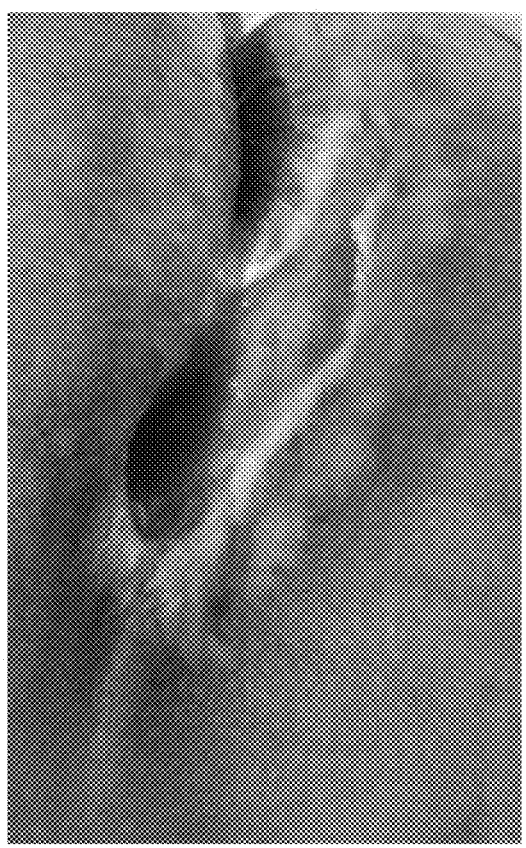
Figure 13G:
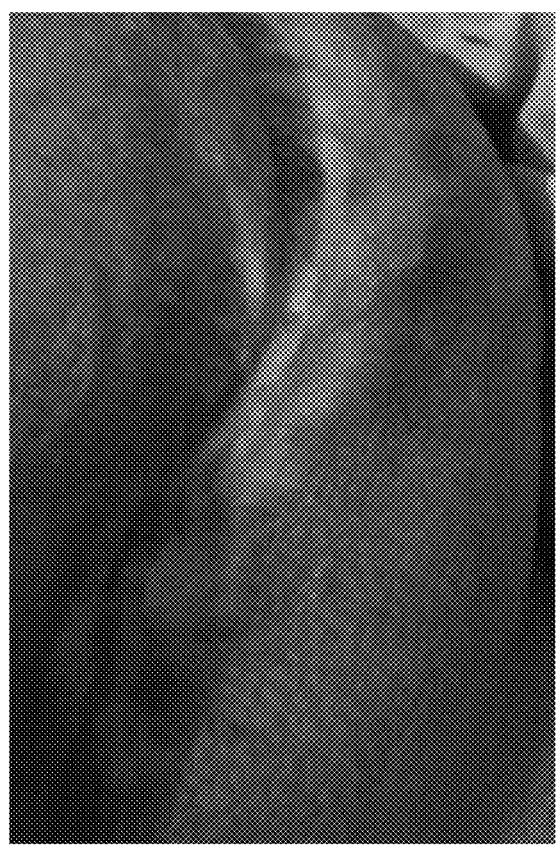

With reference to FIGS. 12E-12I, after substantial closure of the wound, the subject patient was be treated daily with 4 ml-10 ml arnica-inclusive water-based treatment composition and 3 ml-5 ml oil-based treatment composition. After such applications, the injury was wrapped in a gauze impregnated with 4 g-6 g wax-based treatment composition to promote cicatrization. After an additional 4-5 weeks of this second treatment phase, the wound was almost entirely healed, as shown in FIGS. 12H-12I.

In a ninth treatment example, a progression of treatment of bed sore on a patient's coccyx and upper buttocks is sequentially depicted in FIGS. 13A-13H. The subject patient was bedridden for more than two years. Approximately 15 days passed between each respective picture. During the depicted course of treatment, 1 ml-3 ml arnica-free water-based treatment composition was applied to affected area 4-5 times per day and permitted to dry. 3 ml-5 ml oil-based treatment composition was applied at night and covered with gauze. As may be observed, the injury is substantially healed in FIG. 13H.

Although the foregoing embodiments have been described in detail by way of illustration and example for purposes of clarity of understanding, it will be readily apparent to those of ordinary skill in the art in light of the description herein that certain changes and modifications may be made thereto without departing from the spirit or scope of the disclosure. It is also to be understood that the terminology used herein is for the purpose of describing particular aspects only, and is not intended to be limiting, since the scope of the present invention will be limited only by claims submitted in an application which claims priority to the instant application.

It is noted that, as used herein, the singular forms "a", "an", and "the" include plural referents unless the context clearly dictates otherwise. It is further noted that the claims in an application that claims priority to the instant disclosure may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of ordinary skill in the art upon reading this disclosure, each of the individual aspects described and illustrated herein has discrete components and features which may be readily separated from or combined with the features of any of the other several aspects without departing from the scope or spirit of the disclosure. Any recited method can be carried out in the order of events recited or in any other order that is logically possible. Accordingly, the preceding merely provides illustrative examples. It will be appreciated that those of ordinary skill in the art will be able to devise various arrangements which, although not explicitly described or shown herein, embody the principles of the disclosure and are included within its spirit and scope.

Furthermore, all examples and conditional language recited herein are principally intended to aid the reader in understanding the principles of the invention and the concepts contributed by the inventors to furthering the art, and are to be construed without limitation to such specifically recited examples and conditions. Moreover, all statements herein reciting principles and aspects of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary configurations shown and described herein.

In this specification, various preferred embodiments have been described with reference to the accompanying drawings. It will be apparent, however, that various other modifications and changes may be made thereto and additional embodiments may be implemented without departing from the broader scope of this disclosure. The specification and drawings are accordingly to be regarded in an illustrative rather than restrictive sense.

I claim:

1. A composition consisting essentially of-comprising:
   a liquid base;
   arnica plant concentrate; and
   carbolic acid.

2. The composition of claim 1, wherein:
   the composition includes 2-6 ml of arnica plant concentrate per 1 liter of liquid base; and
   the composition includes 1.5-6 ml of carbolic acid per 1 liter of liquid base.

3. The composition of claim 2, wherein:
   the arnica plant concentrate comprises approximately 80% arnica compounds.

4. The composition of claim 2, wherein:
   each 10 ml of arnica plant concentrate contains an amount of arnica compounds corresponding to 0.5 kg-1 kg of fresh arnica plant material.

5. The composition of claim 2, wherein:
   the liquid base includes organic glycerin.

6. The composition of claim 1, wherein:
   the liquid base is glycerin;
   the composition includes 4-6 ml of arnica plant concentrate per 1 liter of glycerin; and
   the composition includes 1.6-3.6 ml of carbolic acid per 1 liter of glycerin.

7. The composition of claim 6, wherein:
   the arnica plant concentrate comprises approximately 80% arnica compounds.

8. The composition of claim 6, wherein:
   each 10 ml of arnica plant concentrate contains an amount of arnica compounds corresponding to 0.5 kg-1 kg of fresh arnica plant material.

9. The composition of claim 2, wherein:
   the liquid base includes substantially comprises distilled water.

10. A composition consisting essentially of:
    a liquid base;
    arnica plant concentrate;
    carbolic acid; and
    essence of oregano.

11. The composition of claim 10, wherein:
    the liquid base is water;
    the composition includes 2-6 ml of arnica plant concentrate per 1 liter of water;

the composition includes 1.2-2.4 ml of carbolic acid per 1 liter of water; and the composition includes 2-6 ml of essence of oregano per 1 liter of water.

12. The composition of claim 11, wherein:

the arnica plant concentrate comprises approximately 80% arnica compounds.

13. The composition of claim 11, wherein:

each 10 ml of arnica plant concentrate contains an amount of arnica compounds corresponding to 0.5 kg-1 kg of fresh arnica plant material.

14. The composition of claim 10, wherein:

the liquid base includes water; and the composition includes 2-6 ml of arnica plant concentrate per 1 liter of water.

15. The composition of claim 10, wherein:

the liquid base includes water; and the composition includes 1.2-2.4 ml of carbolic acid per 1 liter of water.

16. The composition of claim 10, wherein:

the liquid base includes water; and the composition includes 2-6 ml of essence of oregano per 1 liter of water.

17. The composition of claim 10, wherein:

the liquid base includes water;

the composition includes 2-6 ml of arnica plant concentrate per 1 liter of water; and the composition includes 1.2-2.4 ml of carbolic acid per 1 liter of water.

18. The composition of claim 10, wherein:

the liquid base includes water;

the composition includes 1.2-2.4 ml of carbolic acid per 1 liter of water; and the composition includes 2-6 ml of essence of oregano per 1 liter of water.

19. The composition of claim 10, wherein:

the liquid base includes water;

the composition includes 2-6 ml of arnica plant concentrate per 1 liter of water; and the composition includes 2-6 ml of essence of oregano per 1 liter of water.

\* \* \* \* \*